United States Patent
Ehr et al.

(10) Patent No.: US 7,988,718 B2
(45) Date of Patent: *Aug. 2, 2011

(54) STENT CONFIGURATIONS

(75) Inventors: Timothy G. J. Ehr, Elk River, MN (US); Graig L. Kveen, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 211 days.

This patent is subject to a terminal disclaimer.

(21) Appl. No.: 12/260,000

(22) Filed: Oct. 28, 2008

(65) Prior Publication Data

US 2009/0048661 A1    Feb. 19, 2009

Related U.S. Application Data

(63) Continuation of application No. 10/321,089, filed on Dec. 17, 2002, now Pat. No. 7,442,203, which is a continuation of application No. 10/164,989, filed on Jun. 6, 2002, now abandoned, which is a continuation of application No. 09/707,447, filed on Nov. 7, 2000, now Pat. No. 6,471,720, which is a continuation of application No. 09/151,053, filed on Sep. 10, 1998, now Pat. No. 6,193,744.

(51) Int. Cl.
  *A61F 2/06* (2006.01)
(52) U.S. Cl. ..................................... 623/1.15
(58) Field of Classification Search ......... 623/1.13–1.54
  See application file for complete search history.

(56) References Cited

U.S. PATENT DOCUMENTS

| | | |
|---|---|---|
| 5,102,417 A | 4/1992 | Palmaz |
| 5,314,472 A | 5/1994 | Fontaine |
| 5,449,373 A | 9/1995 | Pinchasik et al. |
| 5,507,767 A | 4/1996 | Maeda et al. |
| 5,593,442 A | 1/1997 | Klein |
| 5,613,981 A | 3/1997 | Boyle et al. |
| 5,653,727 A | 8/1997 | Wiktor |
| 5,733,303 A | 3/1998 | Israel et al. |
| 5,735,871 A | 4/1998 | Sgro |
| 5,735,893 A | 4/1998 | Lau et al. |
| 5,755,781 A | 5/1998 | Jayaraman |
| 5,759,192 A | 6/1998 | Saunders |
| 5,776,161 A | 7/1998 | Globerman |
| 5,807,404 A | 9/1998 | Richter |
| 5,810,872 A | 9/1998 | Kanesaka et al. |
| 5,824,043 A | 10/1998 | Cottone, Jr. |
| 5,827,321 A | 10/1998 | Roubin et al. |
| 5,855,600 A | 1/1999 | Alt |
| 5,868,781 A | 2/1999 | Killion |
| 5,876,449 A | 3/1999 | Starck et al. |
| 5,895,406 A | 4/1999 | Gray et al. |

(Continued)

FOREIGN PATENT DOCUMENTS

DE    29701758    3/1997

(Continued)

*Primary Examiner* — Elizabeth Houston
(74) *Attorney, Agent, or Firm* — Vidas, Arrett & Steinkraus, P.A.

(57) ABSTRACT

Improved stent configurations exhibiting limited recoil, resistance to compression and improved longitudinal flexibility are disclosed. The stent comprised of a plurality of annular elements aligned to form a cylindrical stent body. The annular elements are comprised of a plurality of open, generally boomerang-shaped segments interconnected top-to-bottom around each of the annular elements. Adjacent annular elements are interconnected by interconnecting element.

16 Claims, 9 Drawing Sheets

U.S. PATENT DOCUMENTS

| | | | |
|---|---|---|---|
| 5,897,588 A | 4/1999 | Hull et al. | |
| 5,902,332 A | 5/1999 | Schatz | |
| 5,911,754 A | 6/1999 | Kanesaka et al. | |
| 5,922,021 A | 7/1999 | Jang | |
| 5,928,280 A | 7/1999 | Hansen et al. | |
| 5,931,867 A * | 8/1999 | Haindl | 623/1.15 |
| 5,938,682 A | 8/1999 | Hojeibane et al. | |
| 5,948,016 A | 9/1999 | Jang | |
| 5,954,743 A | 9/1999 | Jang | |
| 5,980,553 A | 11/1999 | Gray et al. | |
| 6,017,365 A | 1/2000 | Von Oepen | |
| 6,033,433 A | 3/2000 | Ehr et al. | |
| 6,066,169 A | 5/2000 | McGuinness | |
| 6,068,656 A | 5/2000 | Von Oepen | |
| 6,099,561 A | 8/2000 | Alt | |
| 6,113,627 A | 9/2000 | Jang | |
| 6,123,721 A | 9/2000 | Jang | |
| 6,146,417 A | 11/2000 | Ischinger | |
| 6,190,403 B1 | 2/2001 | Fischell et al. | |
| 6,193,744 B1 | 2/2001 | Ehr et al. | |
| 6,193,747 B1 | 2/2001 | Von Oepen | |
| 6,200,334 B1 | 3/2001 | Jang | |
| 6,231,598 B1 | 5/2001 | Berry et al. | |
| 6,235,053 B1 | 5/2001 | Jang | |
| 6,261,319 B1 | 7/2001 | Kveen et al. | |
| 6,331,189 B1 | 12/2001 | Wolinsky et al. | |
| 6,352,552 B1 | 3/2002 | Levinson et al. | |
| 6,355,057 B1 | 3/2002 | De Marais et al. | |
| 6,355,059 B1 | 3/2002 | Richter et al. | |
| 6,398,805 B1 | 6/2002 | Alt | |
| 6,409,761 B1 | 6/2002 | Jang | |
| 6,416,538 B1 | 7/2002 | Ley et al. | |
| 6,423,090 B1 | 7/2002 | Hancock | |
| 6,432,133 B1 | 8/2002 | Lau et al. | |
| 6,443,982 B1 | 9/2002 | Israel et al. | |
| 6,451,049 B2 | 9/2002 | Vallana et al. | |
| 6,461,380 B1 | 10/2002 | Cox | |
| 6,461,381 B2 | 10/2002 | Israel et al. | |
| 6,464,720 B2 | 10/2002 | Boatman et al. | |
| 6,464,722 B2 | 10/2002 | Israel et al. | |
| 6,468,302 B2 | 10/2002 | Cox et al. | |
| 6,471,720 B1 | 10/2002 | Ehr et al. | |
| 6,475,236 B1 | 11/2002 | Roubin et al. | |
| 6,478,816 B1 | 11/2002 | Kveen et al. | |
| 6,485,508 B1 | 11/2002 | McGuinness | |
| 6,497,723 B1 | 12/2002 | Starck et al. | |
| 7,442,203 B2 | 10/2008 | Ehr et al. | |
| 2001/0020183 A1 | 9/2001 | Jang | |
| 2002/0156524 A1 | 10/2002 | Ehr et al. | |
| 2003/0093144 A1 | 5/2003 | Jang | |

FOREIGN PATENT DOCUMENTS

| | | |
|---|---|---|
| DE | 29702671 | 4/1997 |
| DE | 19834956 | 5/1999 |
| EP | 734698 | 10/1996 |
| WO | 9709945 | 3/1997 |
| WO | 9714375 | 4/1997 |
| WO | 9726840 | 7/1997 |
| WO | 9732543 | 9/1997 |
| WO | 9740780 | 11/1997 |
| WO | 9807386 | 2/1998 |
| WO | 9832412 | 7/1998 |
| WO | 9840035 | 9/1998 |
| WO | 9844871 | 10/1998 |
| WO | 9939660 | 3/1999 |
| WO | 9917680 | 4/1999 |

* cited by examiner

STENT CONFIGURATIONS

CROSS-REFERENCE TO RELATED APPLICATIONS

This Application is a continuation of U.S. application Ser. No. 10/321,089, filed Dec. 17, 2002, now U.S. Pat. No. 7,442,203; which is a continuation of U.S. application Ser. No. 10/164,989, filed Jun. 6, 2002, now abandoned; which is a continuation of U.S. application Ser. No. 09/707,447, filed Nov. 7, 2000, now U.S. Pat. No. 6,471,720; which is a continuation application of U.S. application Ser. No. 09/151,053, filed Sep. 10, 1998, now U.S. Pat. No. 6,193,744; all of which are hereby incorporated herein by reference in their entireties.

BACKGROUND OF THE INVENTION

1. Field of the Invention

This invention relates to stents of improved configuration.

2. Brief Description of the Prior Art

Stents are radially expandable endoprosthesis which are typically intravascular implants capable of being implanted transluminally and enlarged radially after being introduced percutaneously. They have also been implanted in urinary tracts and bile ducts. They are used to reinforce body vessels and to prevent restenosis following angioplasty in the vascular system. They may be self-expanding or expanded by an internal radial force, such as when mounted on a balloon.

In the past, stents have been generally tubular but have been composed of many configurations and have been made of many materials, including metals and plastic. Ordinary metals such as stainless steel have been used as have shape memory metals such as Nitinol and the like. Stents have also been made of biodegradable plastic materials. Such stents have been formed from wire, tube stock, etc. Some stents are self-expanding and some are expanded by an interior radial force.

SUMMARY OF THE INVENTION

This invention provides new configurations of the segments making up stents which may be adapted to all of the various types of prior art stents described above and/or known previously in the art. There are numerous advantages to the new configurations. For example, the configurations of the invention limit recoil and add resistance to compression for an expanded stent, among other things. Also, the stents of this invention are longitudinally flexible.

The inventive stents comprise a plurality of annular elements aligned to form a cylindrical stent body. Each annular element, in turn, is comprised of a plurality of open, generally boomerang-shaped segments. The segments are interconnected top-to-bottom around each of the annular elements. Adjacent annular elements are interconnected by one or more interconnecting elements. Each interconnecting element extends from an end of a boomerang-shaped segment in one annular element to an end of a boomerang-shaped segment in an adjacent annular element. In a preferred embodiment an interconnecting element extends from each boomerang-shaped segment in an annular element to a neighboring boomerang-shaped segment in an adjacent annular element.

Interconnecting elements joining adjacent annular elements are desirably U-shaped or zig-zag shaped, although other curvilinear and rectilinear interconnecting elements may also be used.

Adjacent boomerang-shaped segments in an annular element may be interconnected via a link extending from the top of a segment to the bottom of an adjacent segment. The links may range in design from a short, straight connector to any of the shapes described below for the interconnecting elements.

DETAILED DESCRIPTION OF THE PREFERRED EMBODIMENTS

Figure 1:
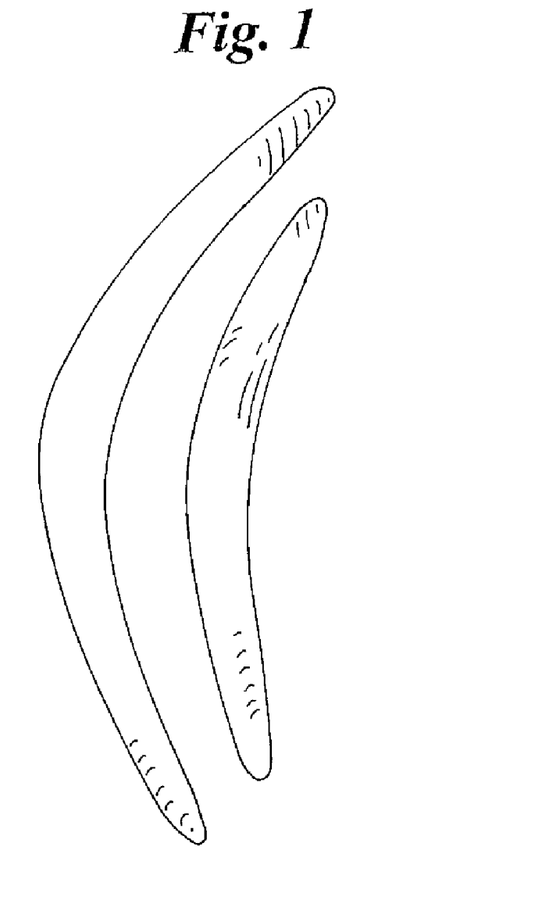
FIG. 1 is a schematic showing boomerang shapes.

For the purposes of this invention, the term boomerang is used to describe the shape of certain stent segments and is used in the sense as described in the *Websters New Collegiate Dictionary* with reference to FIG. 1 hereof:

"boomerang 1: A bent or angular throwing club which can be thrown so as to return near the starting point."

Figure 2:
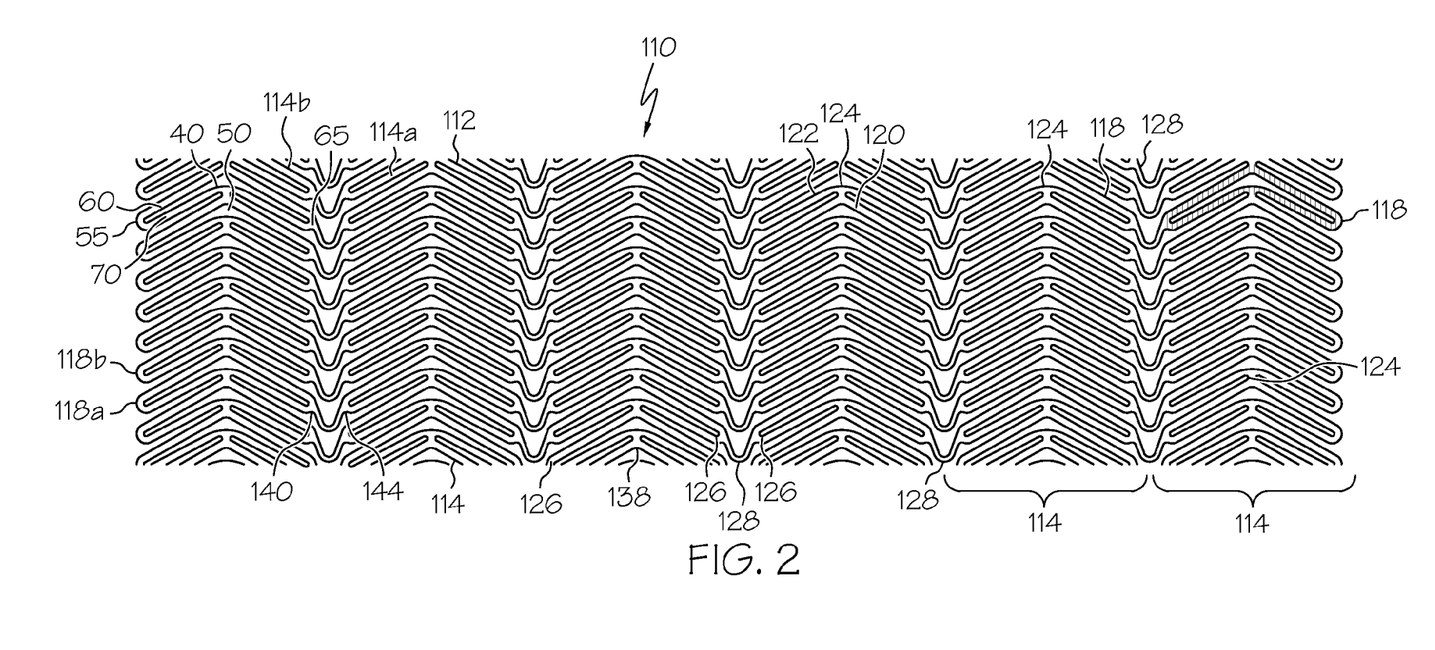
FIG. 2 is a flat plan view of an embodiment of a stent configuration of the invention in the unexpanded condition.
Figure 3:
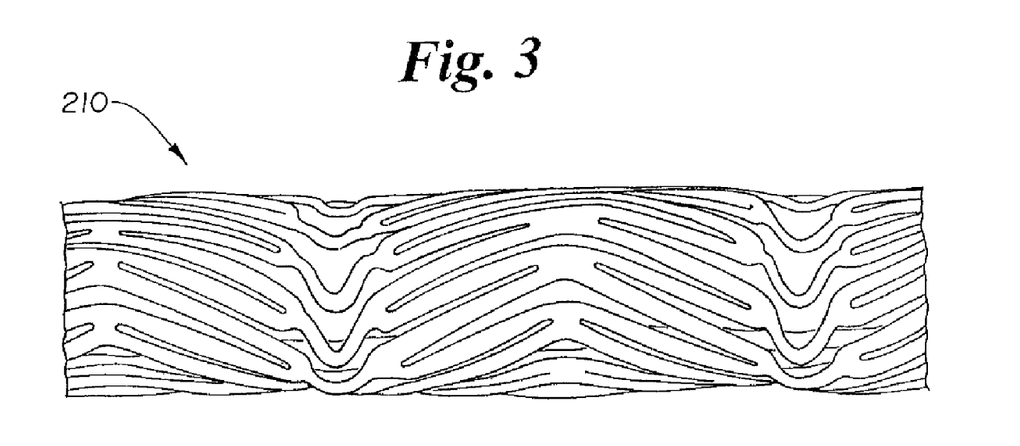
FIG. 3 is a longitudinal view of the stent of FIG. 2 in its normal tubular unexpanded condition.
Figure 4:
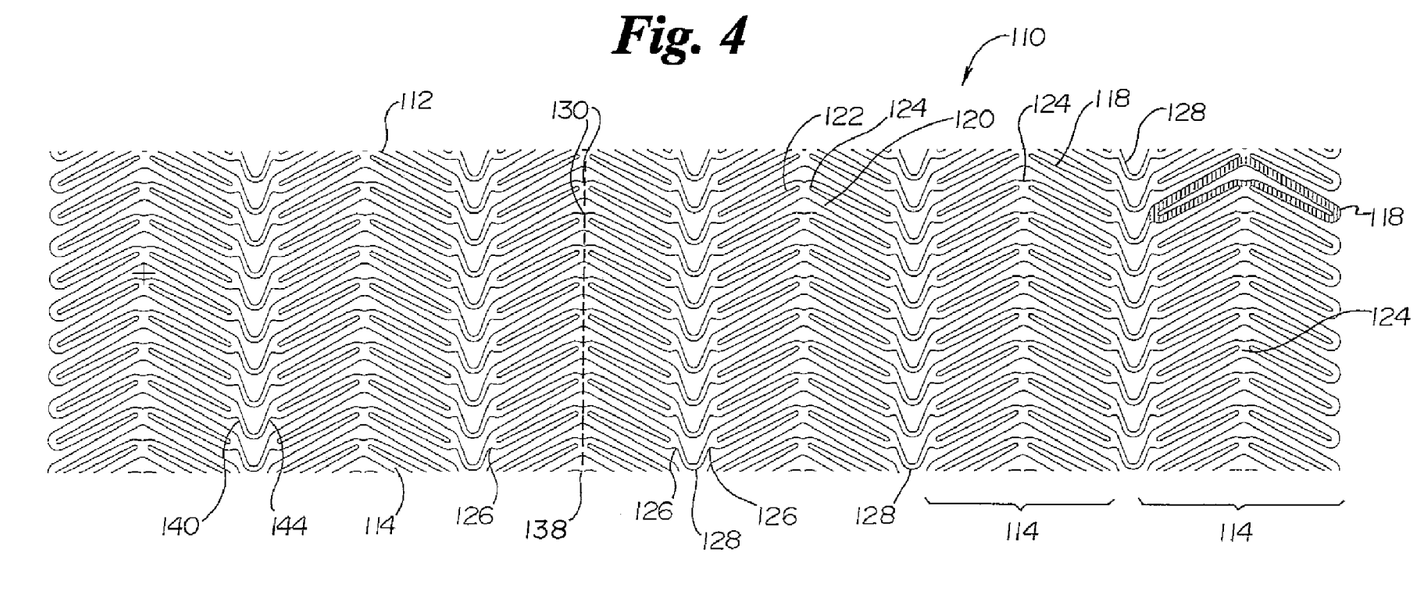
FIG. 4 is a flat plan view of an embodiment of a stent configuration of the invention in the unexpanded condition.

An embodiment of a generally cylindrical stent according to the invention is illustrated in the flat at 110 in FIG. 2 or FIG. 4. The stent may be formed of a metal tube such as nitinol, or stainless steel preferably, which has been etched or preferably laser cut to the configuration shown in the flat plan view of FIGS. 2 or 4. The configuration may be formed in flat sheet and rolled into a cylinder with a welded seam or the like joining together edges 112 and 114, or the configuration may be formed directly in a small tube such as a hypotube. A tubular form of the stent is shown generally at 210 in FIG. 3.

Figure 6:
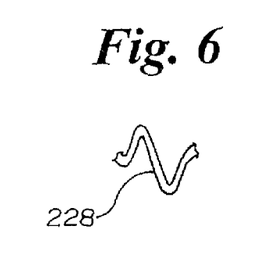
FIG. 6 is an interconnecting element that may be used to join adjacent annular elements in another embodiment of the invention.

The configurations shown in FIGS. 2-4 are made up of a plurality of aligned annular elements 114 aligned as shown to provide a generally cylindrical stent body. Each annular element 114 is comprised of a series of generally boomerang shaped segments indicated at 118 (see darkened segment in the Figures for clarity) having an open structure joined top 120 to bottom 122 at segment junction 124. Segments 118 are arranged or networked as shown in the Figures with ends 126 of neighboring segments on adjacent annular elements joined by interconnecting elements 128. In FIGS. 2-4, interconnecting element 128 is a U-shaped element which is a partly open curve. Alternative interconnecting elements including zig-zag shaped element 228 as shown in FIG. 6, which may be used in place of U-shaped element 128 to join adjacent annular elements 114 together.

The configurations of FIGS. 2 and 4 are substantially similar to one another, differing principally in the presence of a dimple 130 in each bottom 122 of each segment 118 in the configuration of FIG. 4. Without being bound by a particular theory, it is believed that the presence of the dimple limits the extent to which the stent buckles out of the plane on expansion.

It is desirable that the boomerang-shaped segments be at least substantially symmetric about a midline 138 extending from the top 120 of the segment to the bottom 122 of the segment. Midline 138 is situated midway between ends 126 of the segment.

Figure 5:
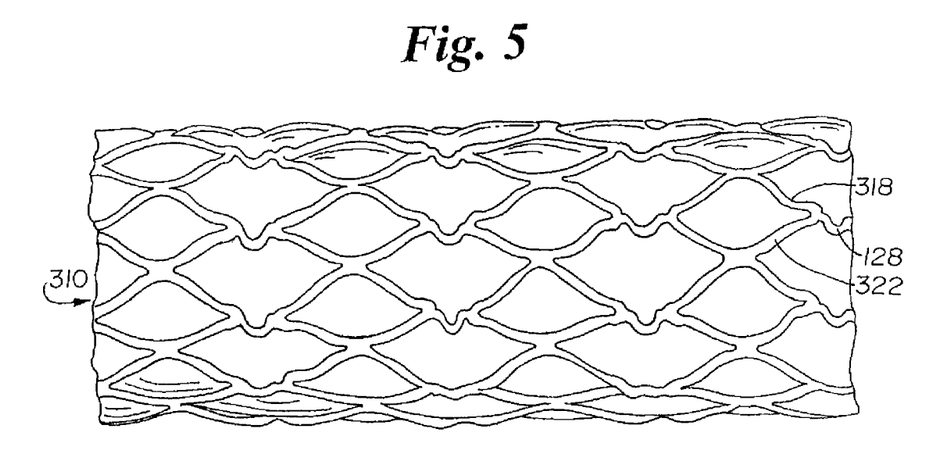
FIG. 5 is a longitudinal view of the stent of FIG. 3 in its tubular, expanded condition.

When the stent of FIG. 2 is expanded, as shown generally at 310 in FIG. 5 on a balloon for example, the boomerang-shaped segments 118 of the unexpanded stent take on a new configuration. The segments 318 take on the shape of rounded triangles with bulging bottoms 322.

It is desirable that the interconnecting elements be U-shaped as shown in FIGS. 2 and 4 or zig-zag shaped as shown in FIG. 6. However, in a more general sense, the invention contemplates the use of curvilinear as well as rectilinear interconnecting elements, including straight elements. Examples of other suitable connectors are disclosed in U.S. patent application Ser. No. 09/111,531 filed Jul. 8, 1998, U.S. patent application Ser. No. 08/846,164 filed Apr. 25, 1997, WO 97/32543 to Divysio Solutions LTD. and WO 97/40780 to David G. Jang, all of which are incorporated herein by reference. Of course, adjacent boomerang-shaped segments may also be joined side-by-side with a region of overlap between adjacent boomerang-shaped segments.

Figure 7:
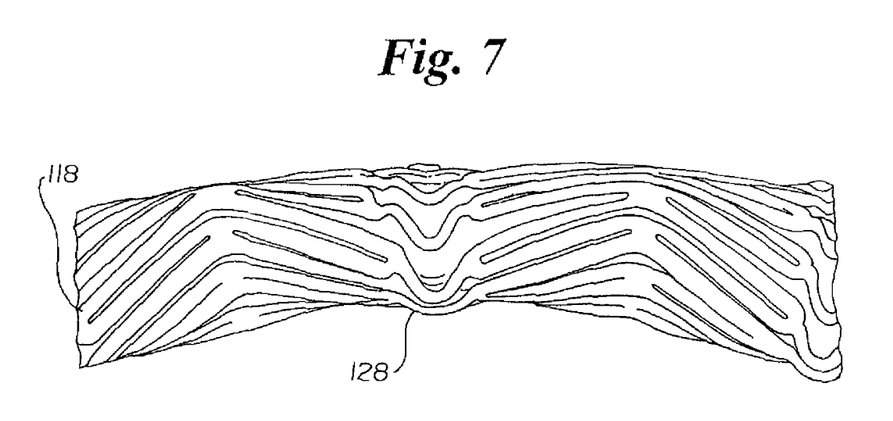
FIG. 7 is a view of the stent of FIG. 3 after being bent.

It is also desirable that interconnecting elements be flexible so as to accommodate bending of the stent without substantial distortion of the boomerang-shaped segments. FIG. 7 shows the stent of FIG. 3 having been bent. As shown in FIG. 7, as the stent is bent, interconnecting elements in tension open while interconnecting elements in compression close to accommodate bending of the stent.

Although as shown in the Figures an interconnecting element extends from each boomerang-shaped segment in an annular element to a nearest neighboring boomerang-shaped segment in an adjacent annular element, the invention further contemplates the possibility of an interconnecting element extending from each boomerang-shaped segment in an annular element to a next-nearest neighboring boomerang-shaped segment in an adjacent annular element. In the latter case, the first end 140 and second end 144 of each interconnecting element 128 would be circumferentially offset along the stent.

In a more general sense, the invention further contemplates a stent in which each adjacent annular element is interconnected by one or more interconnecting elements and each interconnecting element extends from an end of a boomerang-shaped segment in one annular element to an end of a boomerang-shaped segment in an adjacent annular element. As such, an interconnecting element need not extend from each boomerang-shaped segment. An example of this is a stent in which interconnecting elements extend from every second or third boomerang-shaped segment in an annular element.

The invention also contemplates the possibility of altering the orientation of some of the annular elements. In one such embodiment, adjacent annular elements in the flat pattern are rotated by 180° relative to one another so that adjacent annular elements point in opposite directions.

Figure 12:
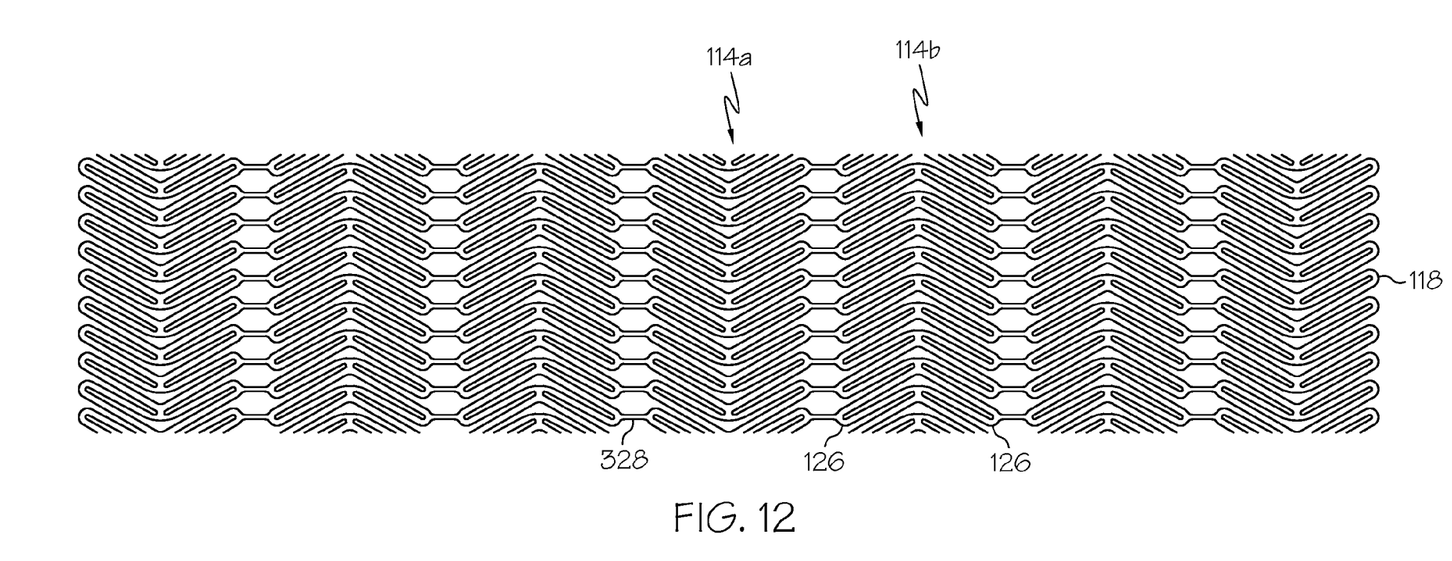
FIG. 12 shows a flat view of an alternate unexpanded stent configuration according to the invention.

For example, FIG. 12 shows annular elements 114a, 114b having an antiparallel chevron pattern. FIG. 12 also shows longitudinally straight connectors 328.

Although the ends of nearest neighboring segments in adjacent annular elements are shown in the figures as aligned with one another along the circumference of the stent, the invention further contemplates embodiments of the stent in which nearest neighboring segments in adjacent annular elements are circumferentially displaced relative to one another.

In yet another series of embodiments, adjacent (or non-adjacent) annular elements may be formed of different sized boomerang-shaped elements. As such, adjacent (or non-adjacent) annular elements may span different lengths. Alternatively, adjacent (or non-adjacent) annular elements may comprise different numbers of boomerang-shaped segments.

Although in the embodiment of FIGS. 2-4, segment junction 124 is shown as a small, straight link extending from the top of one segment to the bottom of an adjacent segment, the invention also contemplates the possibility of adjacent boomerang-shaped segments within an annular element being connected by U shaped links, zig-zag shaped links or any of the shapes disclosed above for the interconnecting elements. Additionally, other shaped segments may be interspersed among the boomerang-shaped segments.

Referring again to FIG. 2, in some embodiments, each annular element 114 can be described as a ring 114 that extends around a circumference of the stent. The boomerang-shaped segments 118 can be described as closed members 118. In some embodiments, a closed member 118 defines a v-shaped opening 50. In some embodiments, a closed member 118 comprises a longer strut 60 and a shorter strut 70 connecting curved peak 55 and valley 65 segments. Each strut 60, 70 can further comprise a curved portion 40 curved substantially symmetrically about a circumference of the stent, such as a circumferential midline 138 of a ring 114.

In some embodiments, the closed members 118 within a ring 114 form a nested chevron pattern. In some embodiments, the struts 60, 70 of the closed members 118 within a ring 114 form a nested chevron pattern. In some embodiments, the closed members 118 and/or the struts 60, 70 of a first ring 114a and a second ring 114b form a parallel chevron pattern relative to one another.

In some embodiments, the shorter strut 70 of a closed member 118 is oriented within a nest defined by the longer strut 60 of the closed member 118. In some embodiments, the longer strut 60 of a first closed member 118a is oriented within a nest defined by the shorter strut 70 of an adjacent closed member 118b.

In some embodiments, adjacent closed members 118 within a ring 114 are connected by a junction 124. In some embodiments, the junctions 124 of a ring 114 are aligned along a circumferential midline 138 of the ring 114.

In some embodiments, the peak segments 55 of one ring 114a are longitudinally aligned with valley segments 65 of another ring 114b. In some embodiments, the peak segments 55 of one ring 114a are longitudinally aligned with peak segments 55 of another ring 114b.

Figure 8:
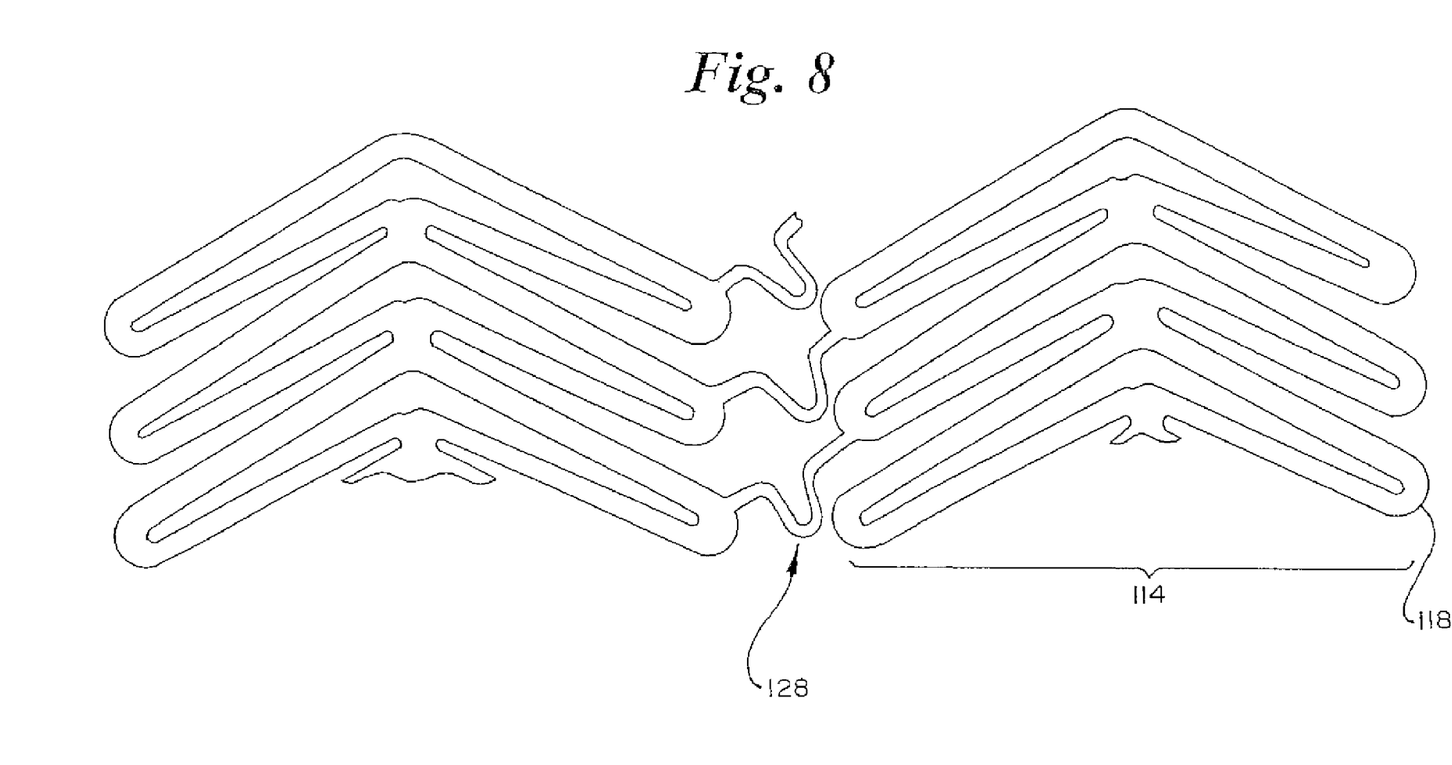
FIG. 8 is a portion of an enlarged flat plan view of an embodiment of the invention in the unexpanded condition.

FIG. 8 illustrates a portion of the configuration of an embodiment of the invention. The embodiment is made of a plurality of aligned annular elements 114. Each annular element 114 is comprised of generally boomerang shaped segments 118. The segments 118 of each annular element 114 are connected via connectors 128. As shown in the embodiment the ends of the connectors are circumferentially displaced from each other.

Figure 9:
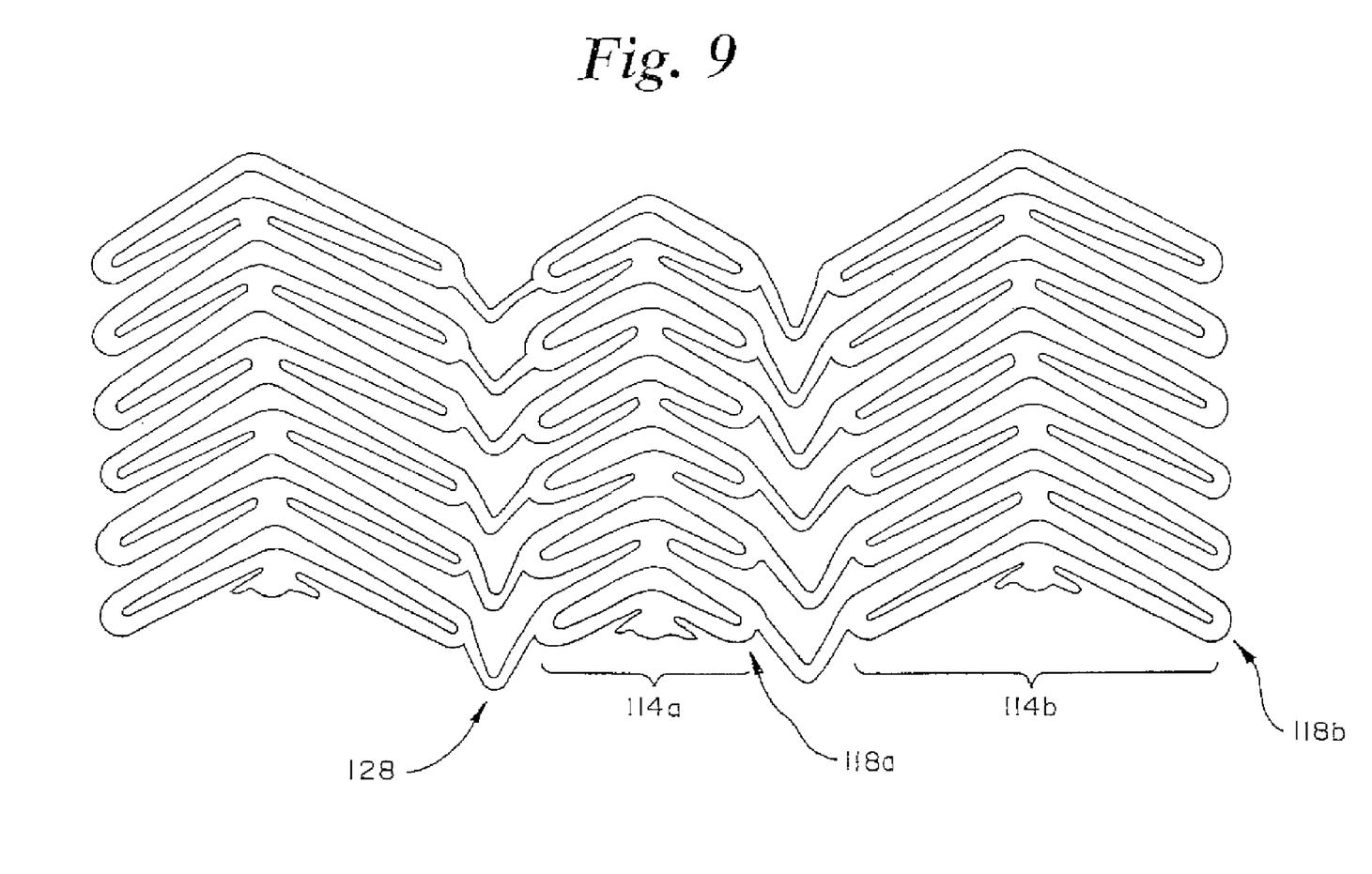
FIG. 9 is a portion of an enlarged flat plan view of an embodiment of the invention in the unexpanded condition.

FIG. 9 illustrates a portion of the configuration of an embodiment of the invention. The embodiment is made of a plurality of aligned annular elements 114. Each annular element 114 is comprised of generally boomerang shaped segments 118. The segments 118 of each annular element 114 are connected via connectors 128. Aligned annular elements 114a and 114b are of different lengths.

Figure 10:
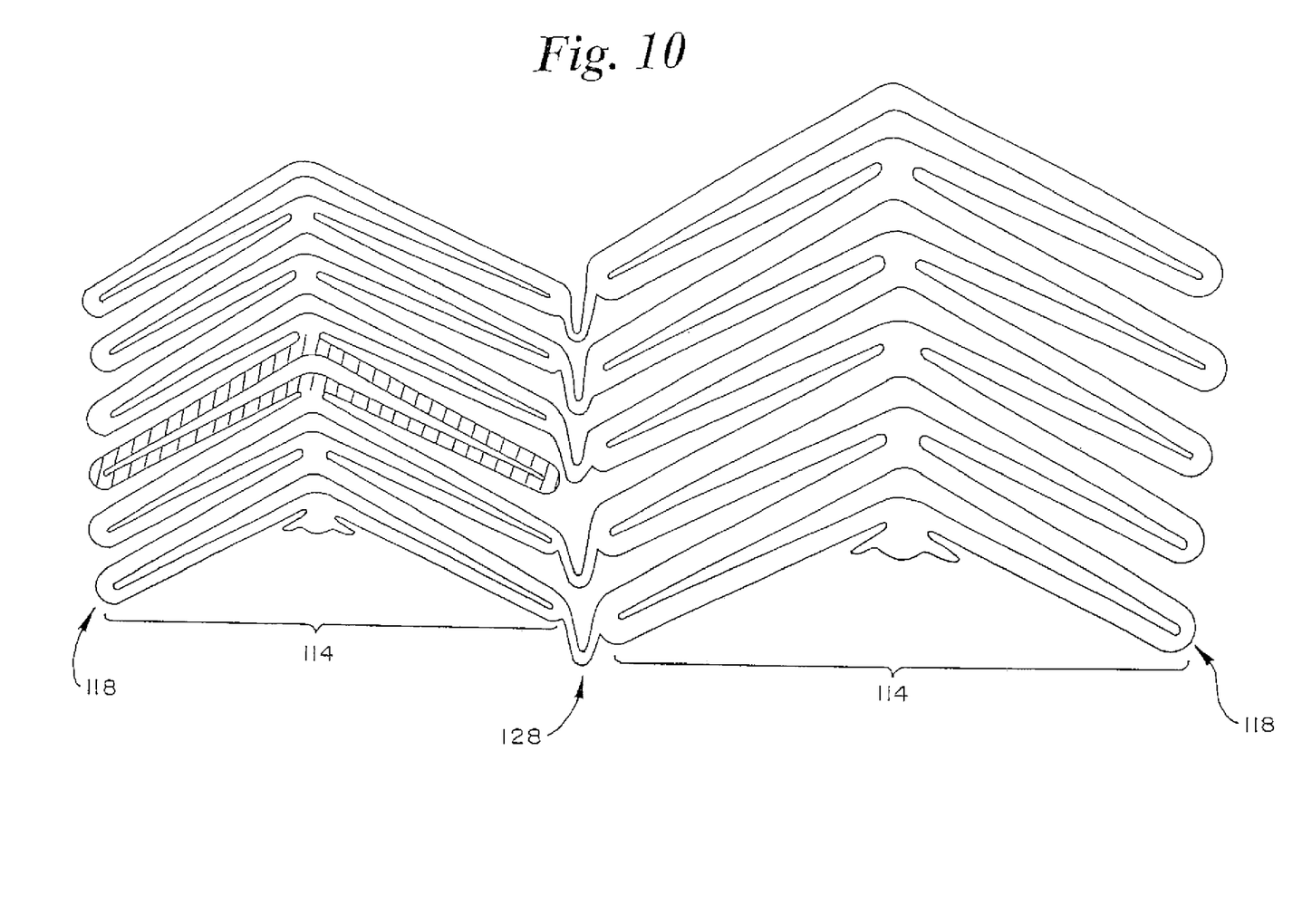
FIG. 10 is a portion of an enlarged flat plan view of an embodiment of the invention in the unexpanded condition.

FIG. 10 illustrates a portion of the configuration of an embodiment of the invention. The embodiment is made of a plurality of aligned annular elements 114. Each annular element 114 is comprised of generally boomerang shaped segments 118. Segments 118 of each annular element 114 are connected via connectors 128. The stent has a first band with a first number of first cells and another first band having a second number of first cells different from the first number.

Figure 11:
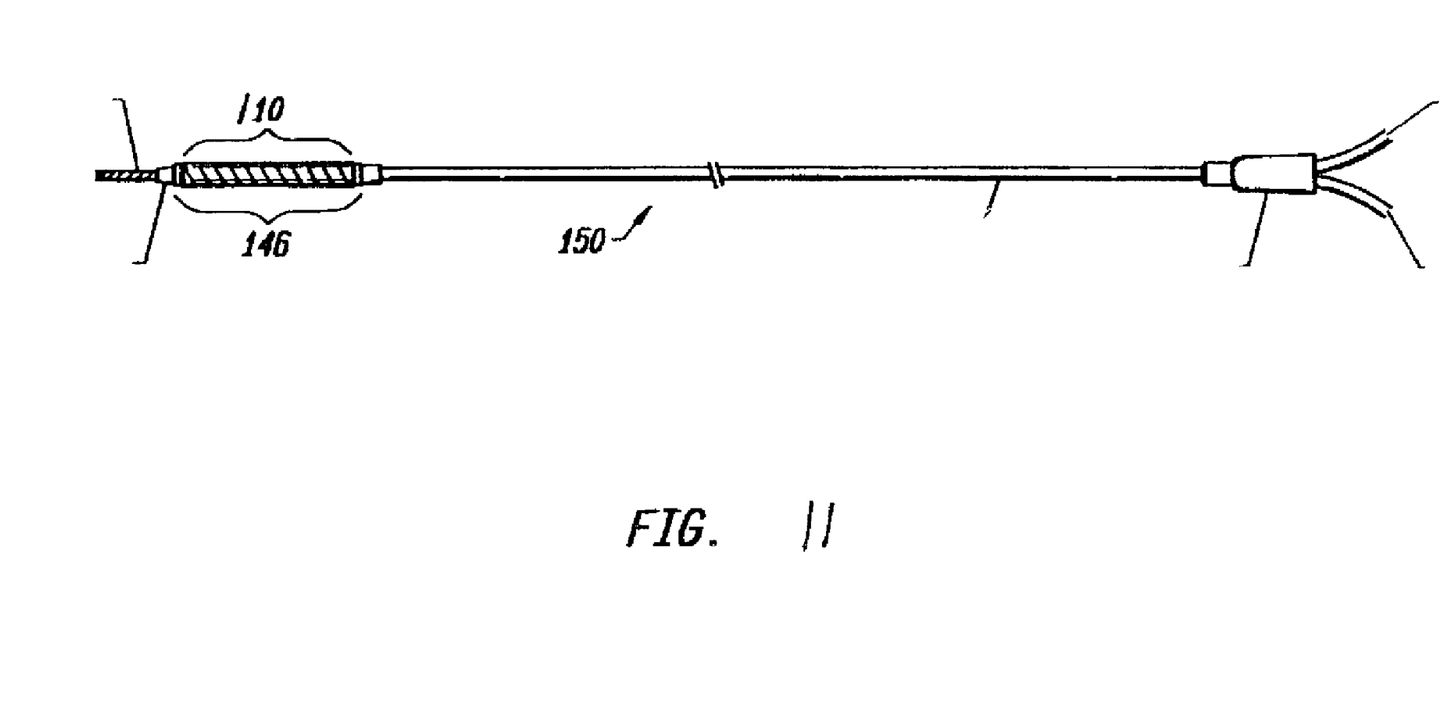
FIG. 11 shows a delivery balloon catheter.

FIG. 11 shows a delivery balloon catheter generally at 150 with stent 110 disposed about balloon 146

The inventive stent may be self-expanding or mechanically expandable such as by balloon. The stent may be made of a variety of suitable bio-compatible materials including metal, plastic and any other material capable of functioning as an expandable stent. For example, the stent may be of metal wire or ribbon such as tantalum, stainless steel or the like or of metal sheeting or metal tubing. It may be thin-walled. It may be of shape memory alloy such as Nitinol or the like.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent comprising:
    an expandable framework defining a plurality of cells, said framework comprising a plurality of adjacent annular elements connected by interconnecting elements, each annular element comprising a plurality of closed segments, each closed segment defining a V-shaped cell, each closed segment comprising a first strut and a second strut, each first and second strut defining a curved portion;
    the V-shaped cells of a first annular element oriented in a first direction, the V-shaped cells of a second annular element oriented in a second direction, each curved portion of the first annular element aligned about a common stent circumference that defines a midline of the first annular element, said midline dividing each V-shaped cell of the first annular element into a first portion and a second portion, the second portion comprising a mirror image of the first portion taken across said midline.

2. The stent of claim 1, wherein the V-shaped cells of a third annular element oriented in the first direction.

3. The stent of claim 2, wherein the V-shaped cells of a fourth annular element oriented in the second direction.

4. The stent of claim 1, wherein the first direction is opposite the second direction.

5. The stent of claim 1, wherein the first direction extends about a circumference of the stent.

6. The stent of claim 1, wherein each closed segment further comprises a peak and a valley.

7. The stent of claim 6, wherein each of the interconnecting elements extend between one of the valleys of the first annular element and one of the peaks of an adjacent annular element.

8. The stent of claim 6, wherein said stent defines a proximal end and a distal end, the peaks of the first annular element located closer to the proximal end than the valleys of the first annular element.

9. The stent of claim 6, wherein each first strut of each closed segment is longer than each second strut.

10. The stent of claim 6, wherein each first strut comprises a V-shape and each second strut comprises a V-shape.

11. The stent of claim 10, wherein each second strut is nested with an adjacent first strut.

12. The stent of claim 10, wherein each first strut and each second strut comprises a proximal portion oriented at an angle to a distal portion.

13. The stent of claim 12, wherein the distal portion of a selected strut of the first annular element is parallel to the proximal portion of a selected strut of the second annular element.

14. The stent of claim 13, wherein the proximal portion of said selected strut of the first annular element is parallel to the distal portion of said selected strut of the second annular element.

15. The stent of claim 7, wherein each valley of the first annular element is connected to one of the interconnecting elements.

16. The stent of claim 1, comprising cells defined by adjacent annular elements and interconnecting elements.

* * * * *